United States Patent [19]
Honke

[11] Patent Number: 6,020,467
[45] Date of Patent: Feb. 1, 2000

[54] ANTIBODIES AGAINST SULFOTRANSFERASE

[75] Inventor: Koichi Honke, Izumi, Japan

[73] Assignee: Takara Shuzo Co., Ltd., Kyoto, Japan

[21] Appl. No.: 09/351,438

[22] Filed: Jul. 12, 1999

Related U.S. Application Data

[62] Division of application No. 09/064,839, Apr. 23, 1998, which is a division of application No. 08/808,641, Feb. 28, 1997, Pat. No. 5,773,274.

[30] Foreign Application Priority Data

Jan. 23, 1997 [JP] Japan ..................... 9-25776

[51] Int. Cl.$^7$ ................................. C07K 16/00
[52] U.S. Cl. ........................................ 530/387.1
[58] Field of Search ........................... 530/387.1

[56] References Cited

U.S. PATENT DOCUMENTS

| | | | |
|---|---|---|---|
| 5,541,095 | 7/1996 | Hirschberg et al. | 435/6 |
| 5,569,830 | 10/1996 | Bennett et al. | 800/205 |
| 5,585,479 | 12/1996 | Hoke et al. | 536/24.5 |

FOREIGN PATENT DOCUMENTS

| | | |
|---|---|---|
| 833483 | 2/1996 | Japan . |
| 8322573 | 12/1996 | Japan . |
| 928374 | 2/1997 | Japan . |

OTHER PUBLICATIONS

Kato et al., *The Journal of Biological Chemistry*, vol. 264, No. 6, pp. 3364–3371 (Feb. 1989).
Spiro et al., *Biochemical Journal*, 319:209–216 (1996).
Kuhns et al., *Glycobiology*, vol. 5, No. 7, pp. 689–697 (1995).
Lo–Guidice et al., *The Journal of Biological Chemistry*, vol. 270, No. 46, pp. 27544–27550 (Nov. 1995).
Skelton et al., *The Journal of Biological Chemistry*, vol. 266, No. 26, pp.17142–17150 (Sep. 1991).
Kobayashi et al., *The Journal of Biological Chemistry*, vol. 271, No. 13, pp. 7645–7653 (Mar. 1996).
Habuchi et al., *The Journal of Biological Chemistry*, vol. 270, No. 8, pp, 4172–4179 (Feb. 1995).
Wlad et al., *The Journal of Biological Chemistry*, vol. 269, No. 40, pp. 24538–24541 (Oct. 1994).
Liu et al., *The Journal of Biological Chemistry*, vol. 271, No. 43, pp. 27072–27082 (Oct. 1996).
Brandan et al., *The Journal of Biological Chemistry*, vol. 263, No. 5, pp. 2417–2422 (Feb. 1988).
Pettersson et al., *The Journal of Biological Chemistry*, vol. 266, No. 13, pp. 8044–8049 (May 1991).
Habuchi et al., *The Journal of Biological Chemistry*, vol. 268, No. 29, pp. 21968–21974 (Oct. 1993).
Rüter et al., *The Journal of Biological Chemistry*, vol. 259, No. 19, pp. 11771–11776 (Oct. 1984).
Chou et al., *The Journal of Biological Chemistry*, vol. 268, No. 1, pp. 330–336 (Jan. 1993).
Hashimoto et al., *The Journal of Biological Chemistry*, vol. 267, No. 22, pp. 15744–15750 (Aug. 1992).
Orellana et al., *The Journal of Biological Chemistry*, vol. 269, No. 3, pp. 2270–2276 (Jan. 1994).
Fukuta et al., *The Journal of Biological Chemistry*, vol. 270, No. 31, pp. 18575–18580 (Aug. 1995).
Honke et al., *J. Biochem.*, 119:421–427 (1996).
Miyao et al., *Urol Res*, 17:317–324 (1989).
Honke et al., *The Journal of Biological Chemistry*, vol. 272, No. 8, pp. 4864–4868 (Feb. 1997).
Uhlmann et al., *Chemical Reviews*, vol. 90, No. 4, pp. 543–584 (Jun. 1990).

*Primary Examiner*—John S. Brusca
*Assistant Examiner*—Andrew Wang
*Attorney, Agent, or Firm*—Birch, Stewart, Kolasch & Birch, LLP

[57] ABSTRACT

An isolated gene encoding a polypeptide possessing sulfotransferase activity which specifically transfers a sulfate group to the C-3-position hydroxyl group of Gal by acting on a sugar chain represented by Gal β1-R, wherein Gal represents galactose; R represents a carbohydrate, lipid or glycoconjugate, and a method for producing the polypeptide.

1 Claim, No Drawings

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 423 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Leu Pro Pro Gln Lys Lys Pro Trp Glu Ser Met Ala Lys Gly
 1               5                  10                  15

Leu Val Leu Gly Ala Leu Phe Thr Ser Phe Leu Leu Val Tyr
                20                  25                  30

Ser Tyr Ala Val Pro Pro Leu His Ala Gly Leu Ala Ser Thr Thr
                35                  40                  45

Pro Glu Ala Ala Ala Ser Cys Ser Pro Pro Ala Leu Glu Pro Glu
                50                  55                  60

Ala Val Ile Arg Ala Asn Gly Ser Ala Gly Glu Cys Gln Pro Arg
                65                  70                  75

Arg Asn Ile Val Phe Leu Lys Thr His Lys Thr Ala Ser Ser Thr
                80                  85                  90

Leu Leu Asn Ile Leu Phe Arg Phe Gly Gln Lys His Arg Leu Lys
                95                  100                 105

Phe Ala Phe Pro Asn Gly Arg Asn Asp Phe Asp Tyr Pro Thr Phe
                110                 115                 120

Phe Ala Arg Ser Leu Val Gln Asp Tyr Arg Pro Gly Ala Cys Phe
                125                 130                 135

Asn Ile Ile Cys Asn His Met Arg Phe His Tyr Asp Glu Val Arg
                140                 145                 150

Gly Leu Val Pro Thr Asn Ala Ile Phe Ile Thr Val Leu Arg Asp
                155                 160                 165

Pro Ala Arg Leu Phe Glu Ser Ser Phe His Tyr Phe Gly Pro Val
                170                 175                 180

Val Pro Leu Thr Trp Lys Leu Ser Ala Gly Asp Lys Leu Thr Glu
                185                 190                 195

Phe Leu Gln Asp Pro Asp Arg Tyr Tyr Asp Pro Asn Gly Phe Asn
                200                 205                 210

Ala His Tyr Leu Arg Asn Leu Leu Phe Phe Asp Leu Gly Tyr Asp
                215                 220                 225

Asn Ser Leu Asp Pro Ser Ser Pro Gln Val Gln Glu His Ile Leu
                230                 235                 240

Glu Val Glu Arg Arg Phe His Leu Val Leu Leu Gln Glu Tyr Phe
                245                 250                 255

Asp Glu Ser Leu Val Leu Leu Lys Asp Leu Leu Cys Trp Glu Leu
                260                 265                 270

Glu Asp Val Leu Tyr Phe Lys Leu Asn Ala Arg Arg Asp Ser Pro
                275                 280                 285

Val Pro Arg Leu Ser Gly Glu Leu Tyr Gly Arg Ala Thr Ala Trp
                290                 295                 300
```

```
Asn Met Leu Asp Ser His Leu Tyr Arg His Phe Asn Ala Ser Phe
                305                 310                 315

Trp Arg Lys Val Glu Ala Phe Gly Arg Glu Arg Met Ala Arg Glu
                320                 325                 330

Val Ala Ala Leu Arg His Ala Asn Glu Arg Met Arg Thr Ile Cys
                335                 340                 345

Ile Asp Gly Gly His Ala Val Asp Ala Ala Ile Gln Asp Glu
                350                 355                 360

Ala Met Gln Pro Trp Gln Pro Leu Gly Thr Lys Ser Ile Leu Gly
                365                 370                 375

Tyr Asn Leu Lys Lys Ser Ile Gly Gln Arg His Ala Gln Leu Cys
                380                 385                 390

Arg Arg Met Leu Thr Pro Glu Ile Gln Tyr Leu Met Asp Leu Gly
                395                 400                 405

Ala Asn Leu Trp Val Thr Lys Leu Trp Lys Phe Ile Arg Asp Phe
                410                 415                 420

Leu Arg Trp
```

(2) INFORMATION FOR SEQ ID NO:2:

(i) SEQUENCE CHARACTERISTICS:
        (A) LENGTH: 1269 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

```
ATGCTGCCAC CGCAGAAGAA GCCCTGGGAG TCCATGGCTA AGGGGCTGGT GCTGGGCGCG      60
CTCTTCACTA GTTTCCTGCT GCTGGTGTAC TCCTATGCCG TGCCCCCGCT GCATGCCGGC     120
CTGGCCTCCA CGACCCCGGA GGCCGCAGCG TCCTGCTCTC CACCTGCACT CGAGCCAGAG     180
GCAGTGATCC GGGCCAACGG CTCGGCGGGG GAGTGCCAGC CGCGGCGCAA CATCGTGTTC     240
TTGAAGACGC ACAAGACGGC CAGCAGCACC CTGCTCAACA TCCTGTTCCG CTTCGGCCAG     300
AAGCACCGGC TCAAGTTCGC CTTCCCTAAC GGCCGCAATG ACTTCGACTA CCCGACCTTC     360
TTCGCCCGCA GCCTGGTGCA GGACTATCGG CCCGGGCCT GCTTCAACAT CATCTGCAAC     420
CACATGCGCT TCCACTACGA CGAGGTGCGC GGCCTGGTGC CGACCAACGC CATCTTCATC     480
ACGGTGCTCC GCGACCCCGC CCGCTTGTTC GAGTCCTCCT TCCACTACTT CGGGCCGGTG     540
GTGCCCCTCA CGTGGAAGCT CTCGGCCGGC GACAAGCTGA CCGAGTTCCT GCAAGACCCG     600
GATCGCTACT ACGACCCCAA CGGCTTCAAT GCCCACTACC TCCGAAACCT GCTCTTCTTC     660
GACCTGGGCT ATGACAACAG CCTGGACCCC AGCAGCCCGC AGGTGCAGGA GCACATCCTG     720
GAGGTGGAGC GTCGCTTCCA CCTGGTGCTC CTTCAAGAGT ACTTCGACGA GTCGCTGGTG     780
CTGCTGAAGG ACCTGCTGTG CTGGGAGCTG AGGACGTGC TCTACTTCAA GCTCAACGCC     840
CGCCGCGACT CGCCCGTGCC GCGGCTCTCG GGGGAGCTGT ATGGGCGCGC CACCGCCTGG     900
AACATGCTGG ACTCCCACCT CTACCGCCAC TTCAACGCCA GCTTCTGGCG CAAGGTGGAG     960
GCCTTCGGGC GGGAGCGCAT GGCCCGCGAG GTGGCCGCCC TGCGCCATGC CAACGAGCGC    1020
ATGCGGACCA TCTGCATCGA CGGGGGCCAC GCCGTGGACG CCGCCGCCAT CCAGGACGAG    1080
GCCATGCAGC CCTGGCAGCC GCTGGGCACC AAGTCCATCC TGGGCTACAA CCTCAAGAAG    1140
AGCATCGGGC AGCGGCACGC GCAGCTCTGC CGGCGCATGC TCACGCCCGA GATCCAGTAC    1200
```

```
CTGATGGACC TCGGCGCCAA CCTGTGGGTC ACCAAGCTCT GGAAGTTCAT TCGCGATTTC    1260

CTGCGGTGG                                                            1269
```

(2) INFORMATION FOR SEQ ID NO:3:

(i) SEQUENCE CHARACTERISTICS:
        (A) LENGTH:  16 amino acids
        (B) TYPE:  amino acid
        (C) STRANDEDNESS:  single
        (D) TOPOLOGY: linear (ii) MOLECULE TYPE: peptide (v) FRAGMENT TYPE: internal fragment (xi) SEQUENCE DESCRIPTION: SEQ ID NO:3:

```
Thr Ala Ser Ser Thr Leu Leu Asn Ile Leu Phe Arg Phe Gly Gln
 1               5                  10                  15

Lys
```

(2) INFORMATION FOR SEQ ID NO:4:

(i) SEQUENCE CHARACTERISTICS:
        (A) LENGTH:   8 amino acids
        (B) TYPE:  amino acid
        (C) STRANDEDNESS:  single
        (D) TOPOLOGY: linear (ii) MOLECULE TYPE: peptide (v) FRAGMENT TYPE: internal fragment (xi) SEQUENCE DESCRIPTION: SEQ ID NO:4:

```
Lys Pro Trp Glu Ser Met Ala Lys
 1               5
```

(2) INFORMATION FOR SEQ ID NO:5:

(i) SEQUENCE CHARACTERISTICS:
        (A) LENGTH:   8 amino acids
        (B) TYPE:  amino acid
        (C) STRANDEDNESS:  single
        (D) TOPOLOGY: linear (ii) MOLECULE TYPE: peptide (v) FRAGMENT TYPE: internal fragment (xi) SEQUENCE DESCRIPTION: SEQ ID NO:5:

```
Ser Ile Leu Gly Tyr Asn Leu Lys
 1               5
```

(2) INFORMATION FOR SEQ ID NO:6:

(i) SEQUENCE CHARACTERISTICS:
        (A) LENGTH:  17 base pairs
        (B) TYPE:  nucleic acid
        (C) STRANDEDNESS:  single
        (D) TOPOLOGY: linear (ii) MOLECULE TYPE: other nucleic acid (synthetic DNA)

(ix) FEATURE:
        (D) OTHER INFORMATION:  N at positions 3, 6 and 15
            is  Inosine (xi) SEQUENCE DESCRIPTION: SEQ ID NO:6:

```
ACNGCNAGYA GYACNCT                                                     17
```

(2) INFORMATION FOR SEQ ID NO:7:

(i) SEQUENCE CHARACTERISTICS:
        (A) LENGTH:  17 base pairs
        (B) TYPE:  nucleic acid
        (C) STRANDEDNESS:  single
        (D) TOPOLOGY: linear (ii) MOLECULE TYPE: other nucleic acid (synthetic DNA)

(ix) FEATURE:
        (D) OTHER INFORMATION:  N at positions 6 and 12 is
            Inosine (xi) SEQUENCE DESCRIPTION:  SEQ ID NO:7:

TTYTGNCCRA ANCGRAA                                                17

(2) INFORMATION FOR SEQ ID NO:8:

(i) SEQUENCE CHARACTERISTICS:
        (A) LENGTH:  47 base pairs
        (B) TYPE:  nucleic acid
        (C) STRANDEDNESS:  single
        (D) TOPOLOGY: linear (ii) MOLECULE TYPE: other nucleic acid (synthetic DNA)

(xi) SEQUENCE DESCRIPTION:  SEQ ID NO:8:

TTCTGGCCRA AGCGGAACAG GATGTTGAGC AGCGTRCTRC TCGCCGT          47

(2) INFORMATION FOR SEQ ID NO:9:

(i) SEQUENCE CHARACTERISTICS:
        (A) LENGTH:  19 base pairs
        (B) TYPE:  nucleic acid
        (C) STRANDEDNESS:  single
        (D) TOPOLOGY: linear (ii) MOLECULE TYPE: other nucleic acid (synthetic DNA)

(ix) FEATURE:
        (D) OTHER INFORMATION:  N at positions 6, 9 and 15
            is
            Inosine (xi) SEQUENCE DESCRIPTION:  SEQ ID NO:9:

AARCCNTGNG ARTCNATGG                                            19

(2) INFORMATION FOR SEQ ID NO:10:

(i) SEQUENCE CHARACTERISTICS:
        (A) LENGTH:  23 base pairs
        (B) TYPE:  nucleic acid
        (C) STRANDEDNESS:  single
        (D) TOPOLOGY: linear (ii) MOLECULE TYPE: other nucleic acid (synthetic DNA)

(ix) FEATURE:
        (D) OTHER INFORMATION:  N at positions 6, 15 and 18
            is Inosine (xi) SEQUENCE DESCRIPTION:  SEQ ID NO:10:
        TTRTANAGRT TRTANCCNAG RAT                                23

(2) INFORMATION FOR SEQ ID NO:11:

(i) SEQUENCE CHARACTERISTICS:
        (A) LENGTH:  6 amino acids
        (B) TYPE:  amino acid
        (C) STRANDEDNESS:  single
        (D) TOPOLOGY: linear (ii) MOLECULE TYPE: peptide (v) FRAGMENT TYPE: internal fragment (xi) SEQUENCE DESCRIPTION: SEQ ID NO:11:

Leu Ser Ala Gly Asp Lys
 1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:12:

Leu Asn Ala Leu Asn Asp Xaa Pro Val
 1               5

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:13:

His Arg Leu Lys
 1

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:14:

Phe Ile Leu Asp Phe Leu Glu Xaa
 1               5

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 3, 6, 9, 12
            and
            15 is Inosine (xi) SEQUENCE DESCRIPTION: SEQ ID NO:15:

ACNGCNTCNT CNACNCT                                                17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 3, 6, 12 and
            15 is Inosine (xi) SEQUENCE DESCRIPTION: SEQ ID NO:16:

ACNGCNAGYT CNACNCT                                                17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 3, 6, 9 and
            15
            is Inosine (xi) SEQUENCE DESCRIPTION: SEQ ID NO:17:

ACNGCNTCNA GYACNCT                                                17

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 6 and 9 is
            Inosine (xi) SEQUENCE DESCRIPTION: SEQ ID NO:18:

AARCCNTGNG ARAGYATGG                                              19

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 2, 8, 14 and
            17 is Inosine (xi) SEQUENCE DESCRIPTION: SEQ ID NO:19:

TNGCCATNGA YTCNCANGG          19

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 2, 14 and 17
            is Inosine (xi) SEQUENCE DESCRIPTION: SEQ ID NO:20:

TNGCCATRCT YTCNCANGG          19

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (synthetic DNA)

(ix) FEATURE:
        (D) OTHER INFORMATION: N at positions 6, 15 and 18
            is Inosine (xi) SEQUENCE DESCRIPTION: SEQ ID NO:21:

TTRTANAGRT TRTANCCNAG RAT          23

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:22:

AAYATYYTNT TYCGNTTYGG          20

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:23:

TTYTGNCCRA ANCGRAA          17

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:24:

AARCCNTGGG ARWSNATGGC                                               20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (synthetic DNA)

(xi) SEQUENCE DESCRIPTION: SEQ ID NO:25:

TTNGCCATNS WYTCCCANGG                                               20

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (synthetic DNA)

(xi) SEQUENCE DESCRIPTION: SEQ ID NO:26:

ATYYTNGGNT AYAAYYTNAA                                               20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (synthetic DNA)

(xi) SEQUENCE DESCRIPTION: SEQ ID NO:27:

TTNARRTTRT ANCCNARRAT                                               20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (synthetic DNA)

(ix) FEATURE:
            (D) OTHER INFORMATION: N at positions 9 and 15 is
                Inosine (xi) SEQUENCE DESCRIPTION: SEQ ID NO:28:

AAYATYYTNT TYCGNTTYGG                                               20

(2) INFORMATION FOR SEQ ID NO:29:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid (synthetic DNA)

(ix) FEATURE:
              (D) OTHER INFORMATION: N at positions 6 and 12 is
                   Inosine (xi) SEQUENCE DESCRIPTION: SEQ ID NO:29:

TTYTGNCCRA ANCGRAA                                                     17

(2) INFORMATION FOR SEQ ID NO:30:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid (synthetic DNA)

(ix) FEATURE:
              (D) OTHER INFORMATION: N at positions 6 and 15 is
                   Inosine (xi) SEQUENCE DESCRIPTION: SEQ ID NO:30:

AARCCNTGGG ARWSNATGGC                                                  20

(2) INFORMATION FOR SEQ ID NO:31:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid (synthetic DNA)

(ix) FEATURE:
              (D) OTHER INFORMATION: N at positions 3, 6 and 18
                   is
                   Inosine (xi) SEQUENCE DESCRIPTION: SEQ ID NO:31:

TTNGCCATNS WYTCCCANGG                                                  20

(2) INFORMATION FOR SEQ ID NO:32:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid (synthetic DNA)

(ix) FEATURE:
              (D) OTHER INFORMATION: N at positions 6, 9 and 18
                   is
                   Inosine (xi) SEQUENCE DESCRIPTION: SEQ ID NO:32:

ATYYTNGGNT AYAAYYTNAA                                                  20

(2) INFORMATION FOR SEQ ID NO:33:

(i) SEQUENCE CHARACTERISTICS:
              (A) LENGTH: 20 base pairs
              (B) TYPE: nucleic acid
              (C) STRANDEDNESS: single
              (D) TOPOLOGY: linear -continued

```
   (ii) MOLECULE TYPE: other nucleic acid (synthetic DNA)

(ix) FEATURE:
          (D) OTHER INFORMATION:  N at positions 3, 12 and 15
              is Inosine (xi) SEQUENCE DESCRIPTION:  SEQ ID NO:33:

TTNARRTTRT ANCCNARRAT                                                  20
```

ANTIBODIES AGAINST SULFOTRANSFERASE

This application is a divisional of co-pending application Ser. No. 09/064,839, filed on Apr. 23, 1998, which is a divisional of application Ser. No. 08/808,641, corresponding to U.S. Pat. No. 5,773,274, the entire contents of which are hereby incorporated by reference.

BACKGROUND OF THE INVENTION

1. Field of the Invention

The present invention relates to a novel sulfotransferase enzyme responsible for sulfation of sugars of glycolipids, the gene encoding said enzyme isolated from a human cell, and production of the sulfotransferase by using an expression vector.

The present invention also relates to methods for control of the expression of sulfotransferase by using an antisense DNA or antisense RNA and methods for detection of sulfotransferase by using a synthetic oligonucleotide probe or primer, as well as an antibody or its fragment.

2. Discussion of the Related Art

In recent years, various physiological functions of the sugar chain moieties of molecules in cell membrane known as complex carbohydrates, such as glycoproteins and glycolipids, have drawn attention. The sulfate group bound to a sugar chain is interesting in terms of various biological functions. The sulfate group is bound to the sugar chains of mucin, mucopolysaccharides and glycolipids in various modes of binding, as well as to the sugar chains of viral glycoproteins, glycoprotein hormones, basement membrane glycoproteins, slime mold lysosome enzymes, etc., via ester linkage. However, its biological significance remains to be elucidated.

Various sulfotransferases of different substrate specificities are already known. For example, sulfotransferases acting on glycoproteins include the sulfotransferase which adds the sulfate group to the 3-position of galactose of N-glycoside type sugar chains [Journal of Biological Chemistry, 264 (6), 3364–3371 (1989)], that which adds the sulfate group to the 6-position of N-acetylglucosamine of N-glycoside type sugar chains [Biochemical Journal, 319, 209–216 (1996)], that which adds the sulfate group to the 3-position of N-acetylgalactosamine of mucin sugar chains [Glycobiology, 5 (7), 689–697 (1995)], that which adds the sulfate group to the 3-position of N-acetylglucosamine of mucin sugar chains [Journal of Biological Chemistry, 270 (46), 27544–27550 (1995)], and that which adds the sulfate group to the 4-position of N-acetylglucosamine of glycoprotein hormone sugar chains produced in the pituitary [Journal of Biological Chemistry, 266 (26), 17142–17150 (1991)].

Sulfotransferases acting on glycosaminoglycans (mucopolysaccharides) include the sulfotransferase which adds the sulfate group to the 2-position of iduronic acid of heparan sulfate [Journal of Biological Chemistry, 271 (13), 7645–7653 (1996)], that which adds the sulfate group to the 6-position of N-sulfated glucosamine of heparan sulfate [Journal of Biological Chemistry, 270 (8), 4172–4179 (1995)], that which adds the sulfate group to the 2-position of iduronic acid of heparin and to the 6-position of N-sulfated glucosamine [Journal of Biological Chemistry, 269 (40), 24538–24541 (1994)], that which adds the sulfate group to the 3-position of N-sulfated glucosamine of heparan sulfate [Journal of Biological Chemistry, 271 (43), 27072–27082 (1996)], that which acts in the N-sulfation of heparan sulfate [Journal of Biological Chemistry, 263 (5), 2417–2422 (1988)], that which acts in the N-sulfation of heparin [Journal of Biological Chemistry, 266 (13), 8044–8049 (1991)], that which adds the sulfate group to the 6-position of N-acetylgalactosamine of chondroitin sulfate and galactose of keratan sulfate and that which adds the sulfate group to the 4-position of N-acetylgalactosamine of chondroitin sulfate [Journal of Biological Chemistry, 268, (29), 21968–21974 (1993)], and that which acts on corneal keratan sulfate only [Journal of Biological Chemistry, 259, (19), 11771–11776 (1984)].

In addition to the sulfotransferase of the present invention, sulfotransferases involved in the synthesis of sugar chains recognized by the monoclonal antibody HNK-1 by adding the sulfate group to the 3-position of glucuronic acid [Journal of Biological Chemistry, 268 (1), 330–336 (1993)] are known to act on glycoplipids.

Of these sulfotransferases, the N-sulfotransferase involved in the synthesis of heparin sugar chains derived from the rat liver [N-heparan sulfate sulfotransferase, Journal of Biological Chemistry, 267 (22), 15744–15750 (1992)], the N-sulfotransferase involved in the synthesis of heparin sugar chains derived from MST cells [N-deacylase/ N-sulfotransferase, Journal of Biological Chemistry, 269 (3), 2270–2276 (1994)], and the enzyme involved in the synthesis of chondroitin sugar chains derived from chick embryo chondrocytes by transferring the sulfate group to the C-6 position of N-acetylgalactosamine [chondroitin 6-sulfotransferase, Journal of Biological Chemistry, 270 (31), 18575–18580 (1995)] are known to act on already cloned complex carbohydrates.

The present inventors purified 3'-phosphoadenosine-5'-phosphosulfate:GalCer sulfotransferase [EC 2.8.2.11] a sulfotransferase which adds the sulfate group to the 3-position hydroxyl group of galactose, from a human renal cancer cell line (SMKT-R3) [Journal of Biochemistry, 119 (3), 421–427 (1996)]. Said sulfotransferase is expressed at high levels in human renal cancer tissue or the cell line thereof, which levels are correlated with the accumulation of sulfated glycolipids in renal cancer. Although this fact suggests a relation between the enzyme and cancer, the enzyme's amino acid sequence remains to be determined and the gene therefor remains to be cloned.

In past attempts of industrially advantageous production of known sulfotransferases, it has been very difficult to isolate the desired sulfotransferase in a pure form by simple procedures and in large amounts because of the low natural abundance of the enzyme and the co-presence of other enzymes, such as proteases and sulfatases.

There is therefore a need for a method for cloning sulfotransferase genes and producing sulfotransferases at low cost and high purity using gene engineering technology. Although cloning of a sulfotransferase gene has been reported as stated above, the number of available reports is very few. Also, because there are a large number of sulfotransferases of different substrate specificities, an attempt to use the sequence of one of the above-mentioned sulfotransferase genes to obtain the gene for another sulfotransferase of different substrate specificity encounters a difficulty in obtaining the desired sulfotransferase gene due to the low gene homology between enzymes of different substrate specificities. Moreover, because the amino acid sequences and gene structures of sulfotransferases acting on glycolipid sugar chains remain unknown, such sulfotransferases are difficult to clone and produce by gene engineering.

Accordingly, the first object of the present invention is to provide a gene encoding a sulfotransferase which particularly expresses in renal cells, at higher levels in renal cancer cells and acts on the sugar chain of glycolipids.

The second object of the present invention is to provide a method for producing a sulfotransferase of high purity which is obtained by genetic engineering using a transformant to which an expression vector containing the preceding gene is introduced.

The third object of the present invention is to provide a polypeptide encoded by the preceding gene.

The fourth object of the present invention is to provide an antisense DNA and antisense RNA complementary to the gene of the present invention or a portion thereof.

The fifth object of the present invention is to provide a synthetic oligonucleotide probe or primer specifically hybridizing to the gene of the present invention.

The sixth object of the present invention is to provide an antibody or a fragment thereof which specifically binds to the polypeptide.

The seventh object of the present invention is to provide a purified sulfotransferase.

These and other objects of the present invention will be apparent from the following description.

SUMMARY OF THE INVENTION

In one embodiment, the present invention relates to an isolated gene encoding a polypeptide possessing sulfotransferase activity which specifically transfers a sulfate group to the C-3-position hydroxyl group of Gal by acting on a sugar chain represented by Galβ1-R, wherein Gal represents galactose; R represents a carbohydrate, lipid or glycoconjugate.

In another embodiment, the present invention relates to a method for producing a polypeptide possessing sulfotransferase activity, comprising the steps of culturing the transformant to which the gene of the present invention is introduced and collecting a polypeptide possessing sulfotransferase activity from the resulting culture.

In still another embodiment, the present invention relates to a polypeptide having sulfotransferase activity encoded by the gene of the present invention.

In still another embodiment, the present invention relates to an antibody or a fragment thereof which specifically binds to the polypeptide of the present invention.

In still another embodiment, the present invention relates to a purified sulfotransferase which acts on a sugar chain represented by Galβ1-R, wherein Gal represents galactose; R represents a carbohydrate, lipid or glycoconjugate, to specifically transfer a sulfate group to the C-3-position hydroxyl group of Gal.

DETAILED DESCRIPTION OF THE INVENTION

As used herein, the statement "possess sulfotransferase activity for specific transfer of the sulfate group to the C-3-position hydroxyl group of Gal by acting on a sugar chain represented by Galβ1-R, wherein Gal represents galactose; R represents a carbohydrate, lipid or glycoconjugate" (hereinafter also referred to as "possess sulfotransferase activity") means the nature characterized by the following action and substrate specificity. Polypeptides possessing such sulfotransferase activity include those having the following physico-chemical properties, and one example is given in the Journal of Biochemistry, 119 (3), 421–427 (1996).

1. Action

Acts on a sugar chain represented by Galβ1-R, wherein Gal represents galactose; R represents a carbohydrate, lipid or glycoconjugate, to specifically transfer the sulfate group to the C-3-position hydroxyl group of Gal.

2. Substrate Specificity

Reacts with galactosyl ceramide (GalCer), lactosyl ceramide (LacCer), galactosyl 1-alkyl-2-acylglycerol (GalAAG), galactosyl diacylglycerol (GalDG), glucosyl ceramide (GlcCer), globotetraosyl ceramide (Gb4Cer), gangliotriaosyl ceramide (Gg3Cer), gangliotetraosyl ceramide (Gg4Cer) and neolactotetraosyl ceramide (nLc4Cer), and does not react with globotriaosyl ceramide (Gb3Cer), galactose and lactose.

3. Optimum pH and Stabilization pH

Optimum pH is about 7.0, and stabilization pH is 6.0 to 8.0.

4. Optimum Temperature and Stabilization Temperature

Optimum temperature is about 37° C., and stability temperature is up to 80° C.

5. Molecular Weight

About 54 kDa, as determined by SDS-PAGE under reducing conditions.

Sulfotransferase activity can be determined by a slightly modified method based on the method described in Analytical Biochemistry, 182, 9–15 (1989). Specifically, 50 μl of a reaction mixture comprising 20 ng of enzyme protein in 5 nmol GalCer, 0.5 μmol $MnCl_2$, 1 nmol [$^{35}$S]PAPS (100 cpm/pmol), 0.5 mg of Lubrol PX, 12.5 nmol dithiothreitol, 0.25 μmol NaF, 0.1 μmol ATP, 20 μg of BSA and 25 mM sodium cacodylate-HCl (pH 6.5) is prepared. After the mixture is incubated at 37° C. for 30 min, the reaction is stopped by the addition of 1 ml of chloroform/methanol/water (30:60:8). The reaction product is isolated using DEAE-Sephadex A-25, and radioactivity is determined using a liquid scintillation counter. One unit of activity is defined as the amount of enzyme that transfers 1 μmol sulfate group per min. If the reaction product exhibits an activity of not lower than $1 \times 10^{-7}$ milliunit, as determined by this method, the product is judged to possess sulfotransferase activity.

The term "gene", as used herein, refers to a gene encoding a polypeptide possessing the above-described sulfotransferase activity, or a gene containing said gene. Specifically, the gene of the present invention is exemplified by the gene encoding a polypeptide comprising the amino acid sequence shown by SEQ ID NO:1 in the sequence listing or a portion thereof, and the gene comprising the nucleotide sequence shown by SEQ ID NO:2 in the sequence listing or a portion thereof. Even genes encoding a polypeptide comprising a portion of the amino acid sequence shown by SEQ ID NO:1 or genes comprising a portion of the nucleotide sequence shown by SEQ ID NO:2 fall within the scope of the present invention, as long as they encode a polypeptide possessing sulfotransferase activity. These are genes for 3'-phosphoadenosine-5'-phosphosulfate:GalCer sulfotransferase [EC 2.8.2.11] derived from human renal cancer cell line SMKT-R3, but the present invention is not limited to them. Any genes, even derived from microorganisms, such as bacteria, yeasts, filamentous fungi, ascomicotina and basidomycotina, plants, and animals, as well as from other human tissues, are included in the scope of the present invention, as long as they encode a polypeptide possessing similar sulfotransferase activity. The present invention also covers variants of the above-mentioned genes that encode a polypeptide possessing functionally similar sulfotransferase activity. For example, any genes encoding a polypeptide resulting from deletion, addition, insertion or replacement of one to several amino acid residues in the amino acid sequence shown by SEQ ID NO:1 in the sequence listing are included in the genes of the present invention, as long as they encode a polypeptide possessing sulfotransferase activity. In short, not only those genes isolated from natural sources but also artificially prepared genes are included in the scope of the present invention, as long as they encode a polypeptide possessing sulfotransferase activity.

Also, those genes encoding a polypeptide capable of hybridizing with a gene of the present invention under stringent conditions, and possessing sulfotransferase activity, are also included in the genes of the present invention.

The statement "under stringent conditions", as used herein, means, for example, the conditions shown below. Specifically, incubation is conducted at 50° C. for 4 hours to over night in 6×SSC (1×SSC=0.15 M NaCl, 0.015 M sodium citrate, pH 7.0) containing 0.5% SDS, 5×Denhardt's [Denhardt's=0.1% bovine serum albumin (BSA), 0.1% polyvinylpyrrolidone, 0.1% Ficoll 400] and 100 μg/ml salmon sperm DNA.

In the present invention, recombinant DNA is DNA obtained by gene engineering techniques, as containing the gene of the present invention.

In the present invention, an expression vector is a vector constructed by inserting the above-described recombinant DNA so that it is expressed in the desired host cell. Vectors incorporating the antisense DNA described below are also included in the expression vectors of the present invention. The vector inserted may be a plasmid vector or phage vector. Useful plasmid vectors include, but are not limited to, pUC18, pUC19, pBluescript, pT7 and other commercially available products; useful phage vectors include, but are not limited to, λgt10 and λgt11 lambda phage vectors and other commercially available products. Host cells include microorganisms, animal cells and plant cells, and are chosen as appropriate according to the expression vector used.

In the present invention, a transformant is a cell obtained by introducing the above-described expression vector into the above-described host cell, which expresses the gene of the present invention.

Expression vector introduction can be achieved by, for example, the method described in Molecular Cloning, A Laboratory Manual, T. Maniatis et al., eds., published by Cold Spring Harbor Laboratory, 1982, pp. 249–254. Next, to select a transformant that expresses the desired gene, characteristics of the expression vector are utilized. For example, when the plasmid vector is pbluescript and the host cell is *Escherichia coli*, a colony incorporating the foreign gene is isolated by selecting an ampicillin-resistant colony on an ampicillin-containing plate, or an ampicillin-resistant white colony on a plate containing ampicillin, 5-bromo-4-chloro-3-indolyl-β-D-galactoside (X-Gal) and isopropyl-β-D-thiogalactopyranoside (IPTG).

The present invention provides a method for producing a polypeptide possessing sulfotransferase activity from the culture obtained by culturing the above-described transformant under such conditions that the gene of the present invention is expressed and the polypeptide encoded by said gene is produced.

Provided that expression of the desired sulfotransferase is recognized, the sulfotransferase can be efficiently produced by optimizing the transformant culture medium composition, medium pH, culturing temperature, the amount and the time of inducer used, culturing period and other conditions for expression of the sulfotransferase.

The sulfotransferase can be purified from the transformant culture using known methods. When the transformant intracellularly accumulates the expression product, as in *Escherichia coli*, the transformant is collected by centrifugation after completion of cultivation, then disrupted by ultrasonication, or the like, followed by centrifugation etc., to yield a cell-free extract. By ordinary protein purification processes, such as salting-out, gel filtration, and hydrophobic, affinity and other various chromatographies, the desired sulfotransferase can be purified from said extract. In the case of some host-vector systems, the expression product is secreted out of the transformant. In this case, it can be purified from the culture supernatant in the same manner as above.

In the case of some host-vector systems, the polypeptide expressed in the transformant is accumulated as an insoluble substance (inclusion body). In this case, the insoluble substance can be recovered and solubilized under mild conditions, such as treatment with a denaturant, e.g., urea, followed by denaturant removal, to restore the original activity.

Although the exogenous sulfotransferase produced by the transformant is co-present with various endogenous sulfotransferases in the host cell, its purification is very easy because its amount is in excess of the amount of endogenous sulfotransferases. Also, when the sulfotransferase is secreted out of the transformant, medium components etc. are co-present but they are normally almost free of protein components that interfere with sulfotransferase purification, an aspect advantageous in that its purification does not necessitate pains-taking procedures for separation, in comparison with sulfotransferase purification from SMKT-R3 cells.

In the case of a sulfotransferase of eukaryotic origin, the enzyme itself can have a sugar chain. In such case, a polypeptide possessing sulfotransferase activity but having no sugar chain can be produced using a host cell incapable of a sugar chain biosynthesis, e.g., a prokaryote, such as *Escherichia coli, Bacillus subtilis* or Actinomycete, or a variant yeast, fungal, animal, insect or plant cell that has lost the capability of a sugar chain biosynthesis. Moreover, a sugar chain can be added to the enzyme itself. In this case, a polypeptide possessing sulfotransferase activity and having a sugar chain can be produced using a host cell capable of a sugar chain biosynthesis, e.g., a yeast, fungus, animal, insect or plant cell.

The polypeptide of the present invention is a polypeptide encoded by the above-described gene of the present invention, and possessing sulfotransferase activity, exemplified by those having the above-mentioned various physicochemical properties. Specifically, the polypeptide of the present invention is exemplified by naturally-occurring sulfotransferase polypeptide having the amino acid sequence shown by SEQ ID NO:1 or a polypeptide comprising a portion thereof, and polypeptides resulting from deletion, addition, insertion or replacement of one to several amino acid residues in the amino acid sequence shown by SEQ ID NO:1.

In the present invention, "antisense DNA" and "antisense RNA" are defined as having a nucleotide sequence complementary to the sulfotransferase gene of the present invention or a portion thereof and suppressing or regulating the expression of gene information (transcription, translation) from an endogenous sulfotransferase gene (genomic DNA and mRNA) by forming a double-stranded structure with the gene. The length of antisense DNA or antisense RNA is variable according to nucleotide sequence specificity and the method for introduction into cells. Antisense DNA or antisense RNA can be prepared by artificial synthesis using a synthesizer, expressing the gene in the direction opposite to the ordinary direction (antisense direction), or the like. For example, a large number of anti-sense techniques are known, concerning the suppression of HIV propagation with the tat gene. [Nucleic Acids Research, 19, 3359–3368 (1991)] or the rev gene [Proceedings of the National Academy of Sciences of the USA, 86, 4244–4248 (1989)]. By these methods, and using the antisense DNA or antisense RNA of the present invention, the expression of an endogenous sulfotransferase gene can be suppressed or regulated. The antisense DNA or antisense RNA of the present invention can also be used as a reagent for laboratory use for in situ hybridization etc.

In the present invention, a synthetic oligonucleotide probe or primer is one that specifically hybridizes to the above-described gene. Said oligonucleotide probe or primer can normally be prepared by artificial synthesis using a synthesizer, or by the PCR method.

In the present invention, any antibody, whether polyclonal or monoclonal, or a fragment thereof serves for the purpose, as long as it specifically binds to the polypeptide of the present invention. The antibody of the present invention can easily be prepared by immunizing rabbits, mice or other animals using the entire or portion of the polypeptide of the present invention by, for example, the method described in Current Protocols in Immunology, John E. Coligan, ed., published by John Wiley & Sons, Inc., 1992. After purification, such an antibody may be treated with peptidase etc. to yield an antibody fragment. Uses of the resulting antibody or a fragment thereof include affinity chromatography, cDNA library screening, and pharmaceuticals, diagnostic, reagents and research reagents.

The present invention is hereinafter descried in more detail by means of an example sulfotransferase derived from SMKT-R3, the human renal cancer cell line described in Urological Research, 17, 317–324 (1989).

The sulfotransferase of the present invention is obtained by first mass-culturing SMKT-R3 cells by the method described in the Journal of Biochemistry, 119 (3), 421–427 (1996), the disclosure of which is herein incorporated by reference, then isolating and purifying the sulfotransferase from the cell culture. Specifically, the purified sulfotransferase of the present invention is produced by the method described below.

SMKT-R3 cells (about $1 \times 10^{10}$ cells) treated with EGF are harvested, washed with PBS, and stored at −80° C. until use. For use, $2.5 \times 10^9$ cells are thawed, suspended in the equal volume of TBS and homogenized briefly with a Potter-type homogenizer. The homogenate is supplemented with the equal volume of 2×solubilization buffer (50 mM Tris-HCl, pH 7.4, 10 mM $MgCl_2$, 2mM β-mercaptoethanol, 2% Lubrol PX, 40% glycerol, 0.5 mM phenylmethylsulfony fluoride, and 0.02 mM E-64) and sonicated for 10 min on ice. After centrifugation, the supernatant obtained is dialyzed against buffer A (10 mM triethanolamine-HCl, pH 7.0, 10% glycerol, and 5mM $MnCl_2$).

The dialyzed material is centrifuged to remove precipitates appearing during dialysis. The supernatant is applied to a DE-52 column, the outlet of which was connected directly to a heparin-Sepharose CL6B column that has been equilibrated with buffer B (10 mM triethanolamine-HCl, pH 7.0, 0.05% Lubrol PX, 10% glycerol, and 5 mM $MnCl_2$). The column was then washed with buffer B until the absorbance of the effluent at 280 nm become less than 0.02. After disconnection of the DE-52 column, the enzyme on the heparin-Sepharose CL6B column is eluted with 0.2 M NaCl in buffer C (20 mM triethanolamine HCl, pH 7.0, 0.1% Lubrol PX, 20% glycerol, and 10 mM $MnCl_2$).

The enzyme-active fractions on heparin-Sepharose chromatography are pooled and dialyzed against buffer B. The dialyzate is applied to a galactosyl sphingosine (GalSph)-Sepharose column which has been equilibrated with buffer B. The column is then washed with buffer B until the eluate is essentially free of protein and the sulfotransferase is eluted with buffer C containing 0.1 M NaCl.

The eluate fractions on GalSph-Sepharose are pooled and dialyzed against 10 mM triethanolamine-HCl (pH 7.0) containing 10% glycerol and applied onto a PLP-Sepharose column connected directly to a HiTrap 3', 5'-bisphosphoadenosine (PAP) column which has been equilibrated with buffer D (10 mM triethanolamine-HCl,pH 7.0, 0.05% Lubrol PX, and 10% glycerol). The column is washed successively with buffer D and buffer B until the eluate is essentially free of protein, then the sulfotransferase is eluted with a linear gradient of 0–0.3 mM PAP in buffer D.

The enzyme-active fractions on HiTrap PAP chromatography are pooled and directly subjected to a second chromatography on a heparin-Sepharose column which has been equilibrated with buffer D. After washing of the column with buffer D, the sulfotransferase of the present invention is eluted in 0.3-ml fractions with buffer C containing 0.3 M NaCl. Through this step, the enzyme preparation is concentrated to about one-fifth of the initial volume, and PAP, which is included in the enzyme preparation from the preceding chromatography, is recovered in the flow-through fractions. The purified enzyme-active fractions are pooled and stored at −80° C. in the presence of 20% glycerol.

Next, information on the partial amino acid sequence of the purified sulfotransferase is obtained. To determine the partial amino acid sequence, the sulfotransferase is subjected directly to amino acid sequencer (Protein Sequencer 476A, produced by Applied Biosystems) by Edman decomposition method [Journal of Biological Chemistry, 256, 7990–7997 (1981)], to determine 10 to 20 N-terminal amino acid residues in the sulfotransferase. Alternatively, the sulfotransferase may be subjected to limited hydrolysis by the action of a highly substrate specific protease, e.g., cichromobacter protease I or N-tosyl-L-phenylalanyl chloromethyl ketone (TPCK)-trypsin, the resulting peptide fragment is separated and purified by reverse-phase HPLC, after which the purified peptide fragment is subjected to amino acid sequencing, to efficiently determine the desired amino acid sequence.

In the present invention, the amino acid sequences of seven peptide fragments are determined: P1 (SEQ ID NO:3), P2 (SEQ ID NO:4), P3 (SEQ ID NO:5), P4 (SEQ ID NO:11), P5 (SEQ ID NO:12), P6 (SEQ ID NO:13) and P7 (SEQ ID NO:14).

On the basis of the partial amino acid sequences thus determined, the sulfotransferase gene of the present invention is cloned. For this purpose, the commonly used PCR method or hybridization method is utilized. The PCR method can be achieved in accordance with the method described in PCR Technology, Erhich, HA, ed., published by Stockton Press, 1989. The hybridization method can be achieved in accordance with, for example, the method described in Molecular Cloning, A Laboratory Manual, 2nd edition, T. Maniatis et al., eds., published by Cold Spring Harbor Laboratory Press, 1989.

However, the sulfotransferase gene of the present invention could not be cloned by the following PCR method using mixed primers (SEQ ID NOs:22–27) (MOPAC method), the MOPAC method using inosine-containing mixed primers (SEQ ID NOs:28–33) or the hybridization method using synthetic oligonucleotides (SEQ ID NOs:22 and 24).

1) PCR Method Using Mixed Primers (MOPAC Method)

This cloning method comprises choosing two regions of low degeneracy in the amino acid sequence determined, synthesizing all possible nucleotide sequence combinations for degenerated codons, and amplifying the desired DNA fragment by PCR using them as a mixed primer.

By this method, the gene encoding uric acid oxidase has been cloned [Science, 239, 1288–1291 (1988)].

The present inventors attempted to obtain the sulfotransferase of the present invention by this method. Various synthetic oligonucleotides were prepared: synthetic oligonucleotides S1 (SEQ ID NO:22) and A1 (SEQ ID NO:23) on the basis of partial amino acid sequence P1 (SEQ ID NO:3), synthetic oligonucleotides S2 (SEQ ID NO:24) and A2 (SEQ ID NO:25) on the basis of partial amino acid sequence P2 (SEQ ID NO:4), and synthetic oligonucleotides S3 (SEQ ID NO:26) and A3 (SEQ ID NO:27) on the basis of partial amino acid sequence P3 (SEQ ID NO:5). Using these synthetic oligonucleotides as a mixed primer, PCR was conducted by a conventional method with SMKT-R3 cell cDNA as a template.

The resulting PCR product was separated by agarose gel electrophoresis. A number of DNA fragments were found to have been amplified, each of which was cut off from the gel, extracted, and incorporated into a plasmid vector, after which its nucleotide sequence was determined by a conventional method (dideoxy chain terminator method) but the sequence likely to be from the desired sulfotransferase gene was not found, although the nucleotide sequences of the synthetic oligonucleotides used as a mixed primer were found.

2) MOPAC Method Using Inosine

This method is similar to the method described in term 1) above but uses a primer resulting from replacement of the third base of a codon of high degeneracy with inosine to reduce the number of mixed primer combinations [Nucleic Acids Research, 16 (22), 10932 (1988)].

Various synthetic oligonucleotides were prepared: synthetic oligonucleotides SI1 (SEQ ID NO:28) and AI1 (SEQ ID NO:29) on the basis of partial amino acid sequence P1 (SEQ ID NO:3), synthetic oligonucleotides SI2 (SEQ ID NO:30) and AI2 (SEQ ID NO:31) on the basis of partial amino acid sequence P2 (SEQ ID NO:4), and synthetic oligonucleotides SI3 (SEQ ID NO:32) and AI3 (SEQ ID NO:33) on the basis of partial amino acid sequence P3 (SEQ ID NO:5). Using these synthetic oligonucleotides as an inosine-containing mixed primer, PCR was conducted by a conventional method with SMKT-R3 cell cDNA as a template.

The nucleotide sequences of the resulting PCR products were determined in the same manner as above but the sequence likely to be from the desired gene was not found, although the nucleotide sequences of the synthetic oligonucleotides used as an inosine-containing mixed primer were found.

3) Hybridization Method Using Synthetic Oligonucleotides

Another commonly used method comprises cloning the desired DNA by designing synthetic oligonucleotides on the basis of amino acid sequence information, and conducting hybridization therewith by a conventional method. The present inventors attempted to detect the sulfotransferase gene of the present invention by this method.

Deduced synthetic oligonucleotides S1 (SEQ ID NO:22) and S2 (SEQ ID NO:24) were prepared from partial amino acid sequences P1 (SEQ ID NO:3) and P2 (SEQ ID NO:4), respectively, and used as probes for plaque hybridization. SMKT-R3 cell cDNA was inserted into a phage vector by a conventional method to yield a cDNA library. *Escherichia coli* infected with this cDNA library was sown over a plate; each plaque obtained was blotted onto a nylon membrane. Hybridization was conducted under commonly used conditions.

As a result, a number of positive plaques were detected in the case of both synthetic oligonucleotides S1 and S2 used as probes. The nucleotide sequences of the DNA inserts in the phage vector of these positive plaques were determined by a conventional method. Although a sequence homologous to the nucleotide sequence of one of the synthetic oligonucleotides used as probes was obtained, the sequence likely to be the desired sulfotransferase gene was not found; the amino acid sequences determined from the nucleotide sequences of the DNA inserts in the phage vectors lacked homology to the above-mentioned partial amino acid sequences.

As stated above, it is very difficult to clone the sulfotransferase gene of the present invention from SMKT-R3 cell cDNA. It is likely that nonspecific DNA fragments are amplified in the PCR method due to inhibition of polymerase reaction, non-specific annealing, or the like, as a result of the tendency for the sulfotransferase gene to take a secondary structure because of high G+C content. In consideration of these aspects, the present inventors made extensive investigation, and attempted to amplify a short gene fragment corresponding to one peptide fragment of known amino acid sequence by the PCR method.

It is preferable that the primer for the PCR method be designed to contain inosine to reduce the number of mixed primer combinations, that a frequently used codon be selected for leucine, and that the primer be synthesized after nucleotide sequence degeneracy is reduced by providing a number of codon combinations for serine. It is thereby possible to amplify a portion of the sulfotransferase gene of the present invention. Next, the present inventors conducted Southern hybridization with this amplified PCR product as a probe, and succeeded in finding a DNA fragment derived from the desired sulfotransferase gene out of the nonspecific DNA fragments obtained.

More specifically, synthetic oligonucleotides 1Sd (SEQ ID NO:6) and 1A (SEQ ID NO:7) are newly prepared on the basis of partial amino acid sequence P1 (SEQ ID NO:3) as primers for the PCR method, and PCR is conducted with SMKT-R3 cell cDNA as a template.

The nucleotide sequence of each PCR product obtained is determined by, for example, the dideoxy chain terminator method [Proceedings of the National Academy of Sciences of the USA, 74 (12), 5463–5467 (1977)]; a nucleotide sequence encoding partial amino acid sequence P1 is found, i.e., a portion of the desired sulfotransferase gene is obtained. On the basis of this nucleotide sequence, synthetic oligonucleotide OP1 (SEQ ID NO:8) is prepared 3'-end labeled by a conventional method, and used as a probe for hybridization.

Also, synthetic oligonucleotides 2Sa (SEQ ID NO:9) and 3A (SEQ ID NO:10) are newly prepared as primers for the PCR method on the basis of partial amimo acid sequences P2 (SEQ ID NO:4) and P3 (SEQ ID NO:5), respectively, and PCR is conducted with SMKT-R3 cell cDNA as a template.

The PCR product obtained is separated by agarose gel electrophoresis, after which it is blotted onto a nylon membrane by a conventional method [Molecular Cloning, A Laboratory Manual, 2nd edition, T. Maniatis et al., eds., published by Cold Spring Harbor Laboratory Press, 1989], followed by hybridization using 3'-end labeled synthetic oligonucleotide OP1. As stated above, hybridization is conducted under stringent conditions, and a DNA fragment that hybridizes to said probe is detected using the detection method appropriate for the label.

As a result, a band which hybridizes with synthetic oligonucleotide OP1 is obtained at a position corresponding to about 600 bp. The nucleotide sequence of this fragment is determined in the same manner as above; sequences corresponding to partial amino acid sequences P1 (SEQ ID NO:3) and P4 (SEQ ID NO:11) of the sulfotransferase are found, demonstrating that portions of the desired sulfotransferase gene are obtained.

Separately, a cDNA library derived from SMKT-R3 cells is prepared. A cDNA library can be prepared using the method described in Chapter 8, Molecular Cloning, A Laboratory Manual, 2nd edition, T. Maniatis et al., eds., published by Cold Spring Harbor Laboratory Press, 1989.

Furthermore, by screening the above-described cDNA library derived from SMKT-R3 cells with the above-described about 600 bp DNA fragment as a probe, a full-length gene encoding the sulfotransferase can be cloned. Also, by screening the genomic DNA library derived from SMKT-R3 cells, genomic DNA of the sulfotransferase of the present invention can also be obtained.

The thus-obtained entire nucleotide sequence of the sulfotransferase gene produced by human renal cancer cell line SMKT-R3 cells is the sequence shown by SEQ ID NO:2 in the sequence listing the entire amino acid sequence encoded thereby is the sequence shown by SEQ ID NO:1 in the sequence listing. Also, this amino acid sequence and nucleotide sequence are new sequences, lacking homology to any known sulfotransferase genes of different substrate specificities.

Because the entire nucleotide sequence of the sulfotransferase gene of the present invention has been clarified, highly homologous DNA to the sulfotransferase gene of the present invention can be cloned by screening genomic DNA or cDNA, or genomic DNA library or cDNA library, derived from an organism other than SMKT-R3 cells, using the entire or portion of the sulfotransferase gene of the present invention as a probe for hybridization.

Also, on the basis of the nucleotide sequence of the sulfotransferase of the present invention, a primer for PCR can be designed. Using this primer, it is possible to detect a highly homologous DNA fragment to the sulfotransferase gene of the present invention from genomic DNA or cDNA, or genomic DNA library or cDNA library, derived from an organism other than SMKT-R3 cells, or to obtain the full-length gene.

To confirm whether the gene obtained is a gene encoding a polypeptide possessing the desired sulfotransferase activity, estimation is possible on the basis of the homology of the nucleotide sequence determined or the amino acid sequence determined to the nucleotide sequence or amino acid sequence of the sulfotransferase of the present invention, respectively. In addition, sulfotransferase activity is determined by the above-described assay method, after the gene product is obtained by above-described method; if an activity is not less than $1 \times 10^{-7}$ milliunit, it is judged that the gene encodes the polypeptide of the present invention.

To produce a functionally equivalent product possessing similar sulfotransferase activity, the following method, for example, can be used. By introducing a random mutation or site-directed mutation into the sulfotransferase gene of the present invention, a gene is obtained which causes deletion, addition, insertion or replacement of one to several amino acid residues in the amino acid sequence of a naturally-occurring sulfotransferase. It is thereby possible to obtain a gene encoding a sulfotransferase possessing the same activity as that of the naturally-occurring sulfotransferase but having slightly different properties, such as optimum temperature, stability temperature, optimum pH and stability pH, and to produce such sulfotransferases by gene engineering.

Methods for random mutagenesis include, for example, the chemical DNA treatment method in which the cytosine base is converted to the uracil base by the action of sodium hydrogen sulfite to cause transition mutation [Proceedings of the National Academy of Sciences of the USA, 79, 1408–1412 (1982)], the biochemical method in which base substitution is caused during double strand synthesis in the presence of [α-S]dNTP [Gene, 64, 313–319 (1988)], and the PCR-based method in which PCR is conducted in the presence of manganese added to the reaction system to reduce the accuracy of nucleotide incorporation [Analytical Biochemistry, 224, 347–353 (1995)].

Known methods for a site-directed mutagenesis include, for example, the method based on amber mutation [gapped duplex method, Nucleic Acids Research, 12 (24), 9441–9456 (1984)], the method utilizing restriction enzyme sites [Analytical Biochemistry, 200, 81–88 (1992); Gene, 102, 67–70 (1991)], the method based on dut (dUTPase) and ung (uracil DNA glycosylase) mutation [Kunkel method, Proceedings of the National Academy of Sciences of the USA, 82 488–492 (1985)], the method based on amber mutation using DNA polymerase and DNA ligase [oligonucleotide-directed dual amber (ODA) method, Gene, 152, 271–275 (1995)], and the method based on PCR using two kinds of primers for mutagenesis with restriction enzyme recognition sites added thereto (U.S. Pat. No. 5,512,463).

Also, using a commercially available kit, a site-directed mutation can easily be introduced. Examples of commercially available kits include Mutan®-G (produced by Takara Shuzo) based on the gapped duplex method, Mutan®-K (produced by Takara Shuzo) based on the Kunkel method, Mutan® -Express Km (produced by Takara Shuzo) based on the ODA method, and the QuikChange™ site-directed mutagenesis kit (produced by STRATAGENE) using a primer for mutagenesis and DNA polymerase derived from *Pyrococcus furiosus*. PCR-based methods also include the TaKaRa LA-PCR in vitro mutagenesis kit (produced by Takara Shuzo) and Mutan®-Super Express Km (produced by Takara Shuzo).

As stated above, the present invention clarifies the primary structure and gene structures of the sulfotransferase derived from human renal cancer cell line SMKT-R3, and allows a method for producing a polypeptide possessing sulfotransferase activity at low cost and high purity by gene engineering.

Moreover, synthetic oligonucleotide probes or primers that specifically hybridize to the sulfotransferase gene of the present invention are useful in the search, detection, amplification, etc. of the sulfotransferase gene of the present invention. An antibody that specifically binds to the polypeptide of the present invention or a fragment thereof is useful in the search, detection, purification, etc. of the sulfotransferase of the present invention.

EXAMPLES

The following examples illustrate the present invention but are not intended to limit the invention in any manner.

Example 1
Purification of Sulfotransferase from SMKT-R3 Cells

SMKT-R3 cells treated with 50ng/ml EGF for 12 to 24 hr were harvested, washed with PBS, and stored at −80° C. until use. For use, 2.5×10$^9$ cells were thawed, suspended in the equal volume of TBS and homogenized briefly with a Potter-type homogenizer. The homogenate was supplemented with the equal volume of 2×solubilization buffer (50 mM Tris-HCl, pH 7.4, 10 mM MgCl$_2$, 2 mM β-mercaptoethanol, 2% Lubrol PX, 40% glycerol, 0.5 mM phenylmethylsulfony fluoride, and 0.02 mM E-64) and sonicated for 10 min on ice. After centrifugation at 100,000×g for 1 hr, the supernatant obtained was dialyzed against buffer A (10 mM triethanolamine-HCl, pH 7.0, 10% glycerol, and 5 mM MnCl$_2$) overnight.

The dialyzed material was centrifuged at 10,000×g for 30 min to remove precipitates appearing during dialysis. No sulfotransferase activity was detected in the precipitates. The supernatant was applied to a DE-52 column (3×20 cm, produced by Whatman), the outlet of which was connected directly to a column (2×10 cm, produced by Pharmacia Biotech) of heparin-Sepharose CL6B that had been equilibrated with buffer B (10 triethanolamine-HCl, pH 7.0, 0.05% Lubrol PX, 10% glycerol, and 5 mM MnCl$_2$). The column was then washed with buffer B at a flow rate of 40 ml/h until the absorbance of the effluent at 280 nm became less than 0.02. After disconnection of the DE-52 column, the enzyme on the heparin-Sepharose CL6B column was eluted with 0.2 M NaCl in buffer C (20 mM triethanolamine-HCl, pH 7.0, 0.1% Lubrol PX, 20% glycerol, and 10 mM MnCl$_2$).

The enzyme-active fractions on heparin-Sepharose chromatography were pooled and dialyzed against buffer B. The dialyzate was applied at a flow rate of 5 ml/h to a GalSph-Sepharose column (1×10 cm, produced by Pharmacia Biotech) which had been equilibrated with buffer B. The column was then washed with buffer B until the eluate was essentially free of protein and the sulfotransferase was eluted with buffer C containing 0.1 M NaCl.

The eluate fractions on GalSph-Sepharose were pooled and dialyzed against 10 mM triethanolamine-HCl (pH 7.0) containing 10% glycerol and applied at a flow rate of 5 ml/h onto a column (1×10 cm, produced by Pharmacia Biotech) of PLP-Sepharose connected directly to a HiTrap PAP column (5-ml bed volume, produced by Pharmacia Biotech) which had been equilibrated with buffer D (10 mM triethanolamine-HCl,pH 7.0, 0.05% Lubrol PX, and 10% glycerol). The column was washed successively with buffer D and buffer B until the eluate was essentially free of protein, then the sulfo-transferase was eluted with a linear gradient of 0–0.3 mM PAP in buffer D.

The enzyme-active fractions on HiTrap PAP chromatography were pooled and directly subjected to a second chromatography on a heparin-Sepharose column (0.3-ml bed volume) which had been equilibrated with buffer D. After washing of the column with buffer D, the sulfotransferase of the present invention was eluted in 0.3-ml fractions with buffer C containing 0.3 M NaCl. Through this step, the enzyme preparation was concentrated to about one-fifth of the initial volume, and PAP, which was included in the enzyme preparation from the preceding chromatography, was recovered in the flow-through fractions. The purified enzyme-active fractions were pooled and stored at −80° C. in the presence of 20% glycerol. The specific activity of the purified enzyme was assayed as described in Example 2 below to be 1.2 units/mg.

Example 2
Action, Substrate Specificity and Physico-Chemical Property of Purified Sulfotransferase The activity of sulfotransferase obtained in Example 1 was assayed as described in Analytical Biochemistry 182, 9–15(1989) with a slight modification. The reaction mixture contained 5 nmol of GalCer, 0.5 μmol of MnCl$_2$, 1 nmol of [$^{35}$S]PAPS (100 cpm/pmol), 0.5 mg of Lubrol PX, 12.5 nmol of dithiothreitol, 0.25 μmol of NaF, 0.1 μmol of ATP, 20 μg of BSA, and enzyme protein in 25 mM Na cacodylate-HCl, pH6.5, in a total volume of 50 μl. In the experiments to examine substrate specificity, 25 nmol of each test glycolipid was used as an acceptor in stead of 5 nmol of GalCer. After incubation at 37° C. for 30 min, the reaction was terminated with 1 ml of chloroform/methanol/water (30:60:8). The reaction product was isolated on a DEAE-Sephadex A-25 column and assayed for radioactivity using a liquid scintillation counter. The values were corrected for a blank value, which was obtained by using the above reaction mixture devoid of the acceptor. One unit of the activity was defined as the amount of enzyme that transferred 1 μmol of sulfate per minute under the above mentioned assay conditions.

TABLE 1

| Substrate | Structure | Relative activity (%) |
|---|---|---|
| GalCer | Gal β Cer | 100 |
| LacCer | Gal β 4Glc β Cer | 61 |
| GalAAG | Gal β AAG | 21 |
| GalDG | Gal β DG | 12 |
| GlcCer | Glc β Cer | 5.9 |
| Gb3Cer | Gal α 4Gal β 4Glc β Cer | 0 |
| Gb4Cer | GalNAc β 3Gal α 4Gal β 4Glc β Cer | <1 |
| Gg3Cer | GalNAc β 4Gal β 4Glc β Cer | 2.8 |
| Gg4Cer | Gal β 3GalNAc β 4Gal β 4Glc β Cer | 3.2 |
| nLc4Cer | Gal β 4GlcNAc β 3Gal β 4Glc β Cer | <1 |

As defined in Table 1, GalCer was the best and LacCer was the second best acceptor under the employed conditions. GalAAG and GalDG also served to some extent as acceptors. The purified sulfotransferase did act on GlcCer, Gb4Cer, Gg3Cer, Gg4Cer, and nLc4Cer, although the relative activities were less than 10% compared with the activity towards GalCer, but did not act on Gb3Cer.

Other Properties of Sulfotransferase of the present invention included that NaCl enhanced the sulfotransferase activity at concentrations up to 0.1 M, but inhibited it at higher concentrations, and that the apparent K$_m$ values of the purified sulfotransferase for GalCer and PAPS were 27 and 25 μM, respectively. The enzyme showed maximum activity between pH 6.5 and 7.0. The purified enzyme could be stored at −80° C. in the presence of 20% glycerol without detectable loss of activity for at least 3 months.

The purified sulfotransferase of the present invention was subjected to SDS-PAGE according to the method of Laemmli [Nature 227, 680–685 (1970)]. In the case of treatment the purified enzyme with sample buffer containing 5% β-mercaptoethanol, it showed a single protein band with a molecular weight of about 54 kDa.

Example 3
Cloning of Sulfotransferase Gene
(1) Construction of cDNA Library

From the above-described SMKT-R3 cell line [Urological Research, 17, 317–324 (1989)], total RNA was extracted [Analytical Biochemistry, 162, 156–159 (1987)], after which poly(A)$^+$ RNA was purified using Oligotex™-dT30 (produced by Takara Shuzo). Double-stranded cDNA was synthesized from the purified poly(A)+ RNA, using the SUPERSCRIPT™ Choice System (produced by Life Technologies). The resulting double-stranded cDNA was combined with an Eco RI adaptor (produced by Life Technologies). This cDNA fragment was ligated with the λgt10 phage vector (produced by Pharmacia Biotech), previously digested with restriction enzyme Eco RI, after which in vitro packaging was conducted using the Ready-To-Go™ Lambda Packaging Kit (produced by Pharmacia Biotech) to yield a λgt10 cDNA library derived from the SMKT-R3 cell line.

(2) Determination of Partial Amino Acid Sequence of Sulfotransferase

Ten micrograms of the sulfotransferase purified in Example 1 was dissolved in a 1 mM EDTA solution (1 ml) containing 6 M guanidium hydrochloride. After 2 µl of 2-mercaptoethanol was added, the test tube was filled with nitrogen and sealed, then incubated at 37° C. for 2 hours for reduction. Ten microliters of 4-vinylpyridine was then added, after which the test tube was filled with nitrogen and sealed, then incubated at 37° C. for 2 hours for S-pyridylethylation.

The pyridylethylated enzyme protein thus obtained was purified by reverse-phase HPLC (RP-HPLC) [system: Waters 625LC, produced by Millipore; column: Cosmosil 5C4-AR-300, 4.6×50 mm, produced by Nacalai Tesque; flow rate: 0.4 ml/min; eluent A: 0.1% trifluoroacetic acid solution (TFA); eluent B: 70% acetonitrile containing 0.1% TFA; elution: conducted on a linear density gradient from 0% to 70% of eluent B over a 55-min period starting at sample application].

The purified S-pyridylethylated enzyme protein (about 2 µg/ml) was dissolved in 400 µl of a 0.1 M Tris-HCl buffer (pH 9.0) containing 3 M urea and digested with 0.3 µg of lysyl endopeptidase (produced by Wako Pure Chemical Industries) at 37° C. for 12 hours.

A peptide fragment was separated and purified from the resulting digest by RP-HPLC [system: Model 130A, produced by Applied Biosystems; column: OD-300C, Aquapore, 7 µm, 1.0×250 mm, produced by Applied Biosystems; flow rate: 0.1 ml/min; eluent A: 0.1% TFA solution; eluent B: 70% acetonitrile containing 0.1% TFA; elution: conducted on a linear density gradient from 0% to 70% of eluent B over an 85-min period starting at sample application].

The peptide fragment thus separated was subjected to amino acid sequencer (Protein Sequencer Model 492, produced by Applied Biosystems) by gas-phase Edman decomposition by a conventional method to determine partial amino acid sequences P1 (SEQ ID NO:3), P2 (SEQ ID NO:4), P3 (SEQ ID NO:5), P4 (SEQ ID NO:11), P5 (SEQ ID NO:12), P6 (SEQ ID NO:13) and P7 (SEQ ID NO:14).

(3) Synthesis of Primers

From the partial amino acid sequences determined in term (2) above, synthetic nucleotides were prepared (DNA Synthesizer Model 392, produced by Applied Biosystems) to yield synthetic nucleotide primers: synthetic nucleotides 1Sa (SEQ ID NO:15), 1Sb (SEQ ID NO:16), 1Sc (SEQ ID NO:17), 1Sd (SEQ ID NO:6) and 1A (SEQ ID NO:7) on the basis of partial amino acid sequence P1 (SEQ ID NO:3), synthetic nucleotides 2Sa (SEQ ID NO:9), 2Sb (SEQ ID NO:18), 2Aa (SEQ ID NO:19) and 2Ab (SEQ ID NO:20) on the basis of partial amino acid sequence P2 (SEQ ID NO:4), and synthetic nucleotides 3S (SEQ ID NO:21) and 3A (SEQ ID NO:10) from partial amino acid sequence P3 (SEQ ID NO:5).

Synthetic oligonucleotide primers 1Sa, 1Sb, 1Sc, 1Sd, 2Sa, 2Sb and 3S are primers for the sense direction, while synthetic oligonucleotide primers 1A, 2Aa, 2Ab, 2A and 3A are primers for the antisense direction.

To prevent mutual binding of primers during hybridization, base substitution with deoxyinosine was conducted in synthesizing all oligonucleotides. Deoxyinosine was substituted in positions where the codon degeneracy was more than 2. For the portion encoding the serine residue, primer combination of the two kinds of codons TCX and AG(T/C) were prepared.

(4) Screening for Sulfotransferase Gene by the RT-PCR Method

In 20 µl of a reaction system containing 2 µg of poly(A)+ RNA extracted from SMKT-R3 cells, 40 µmol oligo(dT)$_{12-18}$ primer (produced by Life Technologies), 0.25 mM (each) dNTP, 50 mM Tris-HCl buffer (pH 8.3), 75 mM potassium chloride, 3 mM magnesium chloride, 10 mM dithiothreitol and 200 units of reverse transcriptase derived from Moloney mouse leukemia virus [SUPERSCRIPT™ II RNase H Reverse Transcriptase, produced by Life Technologies], a reverse transcription reaction was carried out at 37°0 C. for 1 hour. Using a 4 µl aliquot of this reaction mixture as a template, PCR was carried out in 50 µl of a reaction system containing 100 pmol of each of the above-described synthetic oligonucleotide primers (sense direction primers and antisense direction primers), 0.25 mM (each) dNTP mixture, 10 mM Tris-HCl buffer (pH 8.3), 50 mM potassium chloride, 1.5 mM magnesium chloride and 1.25 units of Taq DNA polymerase (produced by Perkin Elmer) (RT-PCR). The reaction was carried out by repeating the sequential treatment at 94° C. for 30 seconds (denaturation), 45–55° C. for 30 seconds (primer annealing) and 72° C. for 1–2 min (synthesis reaction) in 35 cycles.

After this PCR, the entire reaction mixture was subjected to electrophoresis on 2% agarose gel. A DNA fragment was then cut out from the gel and subcloned into the pT7Blue vector (produced by Novagen). The nucleotide sequences of these DNA fragments were determined by the dideoxy chain terminator method using Taq DNA polymerase [Dye Terminator Cycle Sequencing Kit, produced by Perkin Elmer; DNA sequencer model 373A, produced by Applied Biosystems].

RT-PCR was first conducted using four synthetic oligonucleotide primers 1Sa, 1sB, 1Sc and 1Sd for the sense direction and synthetic oligonucleo-tide primer 1A for the antisense direction, resulting in the amplification of a 47 bp cDNA fragment from the combination of 1Sd and 1A and an about 600 bp cDNA fragment from the combination of 2Sa and 3A.

Of these cDNA fragments, the 47 bp cDNA fragment was subcloned and subjected to nucleotide sequencing; the amino acid sequence deduced from the nucleotide sequence determined agreed with partial amino acid sequence P1.

Next, mixed oligonucleotide OP1 (SEQ ID NO:8) was synthesized on the basis of the nucleotide sequence of the 47 bp cDNA fragment, and its 3' end was DIG labeled with terminal transferase using a digoxigenin (DIG) oligonucleotide tailing kit (produced by Boehringer Mannheim).

Using the DIG labeled mixed oligonucleotide OP1 as a probe, Southern blot hybridization was conducted for the about 600 bp cDNA fragment amplified by RP-PCR as described above.

First, the about 600 bp cDNA fragment obtained by RT-PCR was subjected to electrophoresis on 1.5% agarose gel, after which DNA was transferred onto a nylon membrane (produced by Boehringer Mannheim). Using this nylon membrane, hybridization was conducted at 55° C. for 4 hours in a solution containing 2 μmol/ml DIG labeled mixed oligonucleotide OP1, 5×SSC, 2% blocking reagent (produced by Boehringer Mannheim), 0.1% N-lauryl sarcosine and 0.02% SDS. Detection was achieved using a DIG Luminescent Detection Kit (produced by Boehringer Mannheim).

As a result, the OP1 probe hybridized to the about 600 bp cDNA fragment amplified by RT-PCR using synthetic oligonucleotide primers 2Sa and 3A.

This about 600 bp cDNA fragment was subcloned and subjected to nucleotide sequencing; a sequence encoding partial amino acid sequences P1 and P4 was found in this about 600 bp cDNA fragment.

(4) Cloning of cDNA Fragment Containing the Sulfotransferase Gene

To isolate a cDNA clone from the λgt10 cDNA library derived from SMKT-R3 cell line prepared in Example 3 (1), screening was conducted by plaque hybridization.

Using the about 600 bp cDNA fragment obtained in Example 3 (3) as a template, an RNA probe, previously DIG labeled (DIG RNA Labeling Kit, produced by Boehringer Mannheim) using T7 RNA polymerase, was synthesized.

Approximately $2 \times 10^5$ recombinant λ phages and *Escherichia coli* LE392 were mixed to form $2 \times 10^4$ plaques per plate on 10 square plates (9×13 cm). The plaques obtained were transferred onto nylon membranes (produced by Boehringer Mannheim). The membranes were incubated at 4° C. 1 hr, denatured under alkali condition (0.5N NaOH, 1.5M NaCl, 5 min.) and subsequently neutralized (in 0.5M Tris-HCl buffer (pH7.4) containing 1.5M NaCl, 3 min., twice; then in 2×SSC, 2 min., once). Hybridization was carried out at 50° C. overnight with the nylon membranes in a hybridization buffer containing 1 ng of digoxigenin-labeled RNA probe per $cm^2$ of a membrane, 50% formamide, 5×SSC, 2% blocking reagent (produced by Boehringer Mannheim), 0.1% N-laurylsarcosine, and 0.02% SDS. Detection was carried out using DIG Luminescent Detection Kit. Six λ phage clones were picked up from positive plaques and the inserted cDNAs were subcloned into pBluescript vector (produced by Stratagene) by EcoR I digestion.

As a result, a plasmid having a cDNA fragment at most about 1.8 kbp in length was obtained and designated as pBS-hCST1. Its nucleotide sequence was determined; an open reading frame (ORF) encoding a protein consisting of 432 amino acids was found. This ORF contained the entire amino acid sequence determined by partial amino acid sequencer of the above-described purified sulfotransferase.

On the basis of the above results, the entire nucleotide sequence and primary structure of the sulfotransferase gene were determined. The nucleotide sequence encoding the sulfotransferase is shown by SEQ ID NO:2 in the sequence listing, and the amino acid sequence encoded thereby is shown by SEQ ID NO:1 in the sequence listing.

Example 4

Construction of Plasmid for Expression of Sulfotransferase Polypeptide

The plasmid pBS-hCST1 obtained in Example 3 was digested with restriction enzyme Eco RI; the resulting DNA fragment was inserted into the Eco RI site of pSVK3, a vector for expression in mammals (produced by Pharmacia Biotech). The direction of the DNA insert was determined on the basis of the restriction enzyme cleavage map. Two expression plasmids of mutually opposite directions of insertion were designated pSV-hCST and pSV-hCSTR, respectively.

Of these plasmids, pSV-hCST was transformed to *Escherichia coli* JM109 to yield a transformant. This transformant, designated as *Escherichia coli* JM109/pSV-hCST, has been deposited under accession number FERM BP-5811 for *Escherichia coli* JM109/pSV-hcST at the National Institute of Bioscience and Human-Technology, Agency of Industrial Science and Technology.

Example 5

Expression of Recombinant Sulfotransferase Gene in COS-1 Cells $2 \times 10^5$ of COS-1 cells (ATCC CRL 1650) pre-cultured for a day in 35 mm diameter dish were transfected with 1 μg of expression plasmid pSV-hCST or pSV-hCSTR and 5 μl Lipofectamine™ (produced by Life Technologies). After incubation at 37° C. for 72 hr, transformed COS-1 cells obtained were washed twice with cold TBS (20 mM Tris-HCl, 150 mM NaCl, pH7.4), harvested with 0.2 ml TBS containing 0.1% Triton X-100 using a sillicon scraper (produced by Falcon), sonicated on ice to disrupt the cells, and the supernatant was recovered by centrifuging them.

As a result, the specific activity in the cell extract fraction of the COS-1 cells transformed with pSV-hCST was determined to be $1.8 \times 10^{-5}$ U/mg (protein), a level about 16 times the activity in the cell extract fraction of the COS-1 cells having pSVK3 introduced therein as control, and about 8 times the activity in the cell extract fraction of the COS-1 cells transformed with pSV-hCSTR.

Next, it was examined whether the COS-1 cells transfected with pSV-hCST expressed sulfatide or not. The COS-1 cells ($1 \times 10^4$) were transfected with 1 μof pSV-hCST and 1 μl of Lipofectamine in Lab-Tek chamber slide (produced by Nunc Inc.). After incubation at 37° C. for 48 h, the transformed COS-1 cells were washed with PBS (pH7.4), fixed in 1% paraformaldehyde in PBS(pH7.4), blocked with 1% BSA in PBS(pH7.4), and incubated with an anti-sulfatide monoclonal antibody, Sulph 1 [Biochemical Journal, 251 17–22, (1988)], followed by FITC-conjugated goat anti-mouse IgG antibody (produced by Zymed Laboratories). Each incubation time was 45 min. Labeled cells were mounted in Vectashield mounting medium (produced by Vector Labo), and observed using fluorescence and phase microscope.

As a result, it was found that the cell surface was immunofluorescently stained in the COS-1 cells transformed with pSV-hCST, while the untransformed COS-1 cells were not stained at all, demonstrating that the sulfotransferase exhibited its activity to synthesize a sulfatide in the transformed COS-1 cells.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An isolated antibody or fragment thereof which specifically binds to a polypeptide having sulfotransferase activity and comprising SEQ ID NO: 1.

* * * * *